(12) United States Patent
Lee et al.

(10) Patent No.: US 9,618,489 B2
(45) Date of Patent: Apr. 11, 2017

(54) GENERATOR CONDITION MONITORING DEVICE AND METHOD USING GASEOUS DECOMPOSITION PRODUCTS SENSOR

(71) Applicant: POWERCHEMTEC INC., Daejeon (KR)

(72) Inventors: Tae Won Lee, Daejeon (KR); Sung Min Ha, Seoul (KR)

(73) Assignee: POWERCHEMTEC INC., Daejeon (KR)

(*) Notice: Subject to any disclaimer, the term of this patent is extended or adjusted under 35 U.S.C. 154(b) by 133 days.

(21) Appl. No.: 14/553,067

(22) Filed: Nov. 25, 2014

(65) Prior Publication Data

US 2016/0091473 A1   Mar. 31, 2016

(30) Foreign Application Priority Data

Sep. 25, 2014   (KR) .................. 10-2014-0128211

(51) Int. Cl.
*G01N 33/00* (2006.01)

(52) U.S. Cl.
CPC ....... *G01N 33/0011* (2013.01); *G01N 33/005* (2013.01)

(58) Field of Classification Search
CPC .................. G01N 33/0011; G01N 33/005
See application file for complete search history.

(56) References Cited

U.S. PATENT DOCUMENTS

| 3,427,880 A | 2/1969 | Grobel et al. |
| 3,702,561 A * | 11/1972 | Carson ............ G01R 31/343 436/7 |
| 4,436,699 A | 3/1984 | Narato et al. |
| 6,959,585 B2 * | 11/2005 | Brosnihan ............ H02K 9/10 108/50.02 |

FOREIGN PATENT DOCUMENTS

| JP | 2013-521473 A | 6/2013 |
| KR | 10-1209428 B1 | 12/2012 |
| WO | WO 2011/106850 A1 | 9/2011 |

OTHER PUBLICATIONS

Korean Office Action dated Oct. 5, 2015.

* cited by examiner

*Primary Examiner* — Paul West
(74) *Attorney, Agent, or Firm* — Rabin & Berdo, P.C.

(57) ABSTRACT

A generator condition monitoring device using gaseous decomposition products sensor according to the present invention comprises moisture trap and a filter for removing moisture and oil in generator cooling hydrogen gas, three way solenoid valve for changing flow of hydrogen gas, hydrocarbon trap for absorbing and removing gaseous decomposition products in a hydrogen gas, a dew point meter for measuring amount of moisture in hydrogen gas, and detection sensor for detecting gaseous decomposition products in hydrogen gas.

7 Claims, 3 Drawing Sheets

GENERATOR CONDITION MONITORING DEVICE AND METHOD USING GASEOUS DECOMPOSITION PRODUCTS SENSOR

BACKGROUND OF THE INVENTION

1. Field of the Invention

The present invention relates to a device and a method for detecting overheated parts which can cause a catastrophic failure by measuring contents of gaseous decomposition products contained in hydrogen gas which is used as a coolant.

2. Description of the Related Art

Overheating can be occurred in case there is abnormality such as deterioration of insulating material, windings shorted, damaged strands, and partial discharge within a generator or a motor in operation. And adjacent materials such as epoxy, enamel, paint, varnish, insulating material, air, etc. are decomposed by the heat, which produces particulate or gaseous decomposition products.

These produced decomposition materials are contained in cooling gas (hydrogen or air). Thus, occurrence of abnormality can be informed by detecting particulate or gaseous decomposition products contained in the cooling gas of a motor or a generator.

The size of particles produced by decomposition of the adjacent materials such as epoxy, enamel, varnish, and insulating material is 0.001~0.01 μm or so. Currently, the only worldwide product used for monitoring hot spot in generator is GCM, Generator Condition Monitor (also called Generator Core Monitor) which monitors by detecting particulate decomposition using ICD (Ion Chamber Detector) sensor. GCM was developed by GE (General Electronic) in US and has been sold by GE and Environment One Corporation.

ICD detects by charging particulate materials using radiation source (thorium 232). The output of sensor is decreased as the concentration of particulate material is increased. In normal condition, the sensor output is adjusted to be about 80% of full scale. And an alarm is issued if sensor output goes below 50%. GCM have had frequent invalid alarms due to causes not related to generator overheating such as the intrusion of oil from generator sealing oil system and moisture from hydrogen cooling system into generator and low sample gas flow. Thus, it is true that the reliability of the system is low. Although a trap can be installed in the upstream of the detector to remove oil, it also removes the particles together, and decreases the sensitivity of the sensor. Many devices of this type have installed on a number of generators in the country. The devices stopped or removed from the system are increasing due to frequent malfunction.

On the other hand, if there is a hot spot due to abnormality within generator, various gaseous decomposition products (VOCs) are produced. Those produced gaseous decomposition products (VOCs) are shown in Table 1.

TABLE 1

Gaseous decomposition products (VOCs) produced within generator
gaseous decomposition products (VOCs)

1. Heptane
2. Dioxane
3. Toluene
4. Octane
5. Xylene

TABLE 1-continued

Gaseous decomposition products (VOCs) produced within generator
gaseous decomposition products (VOCs)

6. Benzaldehyde
7. Trimethylbenzene
8. Decane
9. Methyldecane
10. Methylphenol
11. Undecane
12. Benzothiazole
13. Bisphenol-A Those produced gaseous decomposition products (VOCs) appear in different amount depending on the size of abnormality, thus abnormality of generator in operation can be determined according to concentration of gaseous decomposition products (gaseous molecules).

In detecting gaseous decomposition products, PID (Photo Ionization Detector) sensor or semiconductor type sensor can be used. PID sensor includes a light source emitting light of short frequency (Ultra Violet), and two electrodes. If the light of UV is irradiated to gaseous molecules, some of molecules are being ionized, i.e. converted into positively charged ions and negatively charged ions. Positively charged ions are attracted to cathode and negatively charged ions are attracted to anode, which makes current flow.

In this process, the flowing current is proportional to the concentration of gaseous decomposition products, thus the concentration of gaseous decomposition products is measured. In a PID sensor, the oil contained in the gas sample (cooling gas introduced to sensor) can pollute the sensor and too much moisture can decrease the sensitivity of the sensor, so they have to be removed before introducing to the sensor. Also when an alarm is issued, it is necessary to check whether warning is due to the actual situation or malfunction of the device.

As a specific prior art, the technology disclosed by Patent Publication No. 10-1209428 dated Nov. 30, 2012 'An apparatus for generator condition monitoring using VOCs sensor'.

In referring to the prior art illustrated in FIG. 1, the prior art comprises a preprocessing module 1 for taking some hydrogen gas (a sample gas) and removing moisture or oil in the hydrogen gas, a filter 2 for removing particles larger than 0.001 μm, flow controller 3 for introducing a certain amount of a gas into the sensor, gaseous decomposition products sensor 6 sensitive to gaseous decomposition products contained in a hydrogen gas, and a signal processing module 7 for issuing warning when the concentration of gaseous decomposition products exceeds the control standard value. And in the detection of gaseous decomposition products it is possible to remove the moisture or oil in a hydrogen gas before introducing the sample gas to the sensor. Thus, malfunction due to moisture or oil can be prevented and this kind of hot spot monitoring system can be more reliable. The oil and moisture which contaminates the sensor or decreases the sensitivity of the sensor are removed by filter and moisture trap respectively, which means the prolonged life of sensor and high sensitivity. Appropriate repair plans can be established and reacted depending on degree of abnormalities by monitoring continuously generator conditions. Thus, it can contribute to stable power supply by preventing unplanned shutdown and reduce maintenance costs.

However, the prior art is configured to have a means to prevent the reason of malfunction in advance, water leak can occur by corrosion of the system since water is used for cooling in the preprocessing module 1. In case the temperature of water is high (in summer), removal of oil or moisture in the actual hydrogen gas is not enough by degraded cooling effect and thereby gaseous decomposition products sensor is contaminated or performance of the device can be degraded by degraded sensitivity of the sensor. Thus, in case an alarm is issued, there is the limit to make operator's decision difficult since there is no means to verify whether warning is due to the actual situation (occurrence of overheated parts), or abnormality of the device.

PRIOR ART DOCUMENTS

Patent Registration No. 10-1209428 (Date: 30 Nov. 2012)
U.S. Pat. No. 3,427,880A, "Overheating detector for gas cooled electric machine", 1972
U.S. Pat. No. 4,436,699A, "Monitoring system for checking electric rotary machine for local overheating", 1984

SUMMARY OF THE INVENTION

The present invention is for improving the problem of the prior art, and generator condition monitoring device and method using gaseous decomposition products (VOCs) sensor are provided, wherein moisture a trap filled with absorbent is used in order to remove oil or moisture and a filter to remove particles in a hydrogen gas in the device for monitoring occurrence of high temperature part by detecting gaseous decomposition products (VOCs). A three way solenoid valve and a dew point meter for monitoring moisture contents in a hydrogen gas are installed to remove moisture by letting the hydrogen gas pass the moisture trap only in case moisture contents in the hydrogen gas exceeds the standard value (relative humidity higher than 35% affects the sensor). And the three way solenoid valve and a hydrocarbon trap for absorbing and removing gaseous decomposition products are installed to verify the validation of alarm. When an alarm is issued, the solenoid valve make the sample gas flow through the hydrocarbon trap for about 5 minutes and return to normal flow path. If the device indicates "0" for a moment and goes back to former value then, it means the real situation. But if the device continues to indicate the same value, it means the device is in the malfunction.

In order to accomplish this objective, a generator condition monitoring device using gaseous decomposition products sensor comprises a gas preprocessing module for extracting some (the sample gas) of a hydrogen gas circulating inside a generator in operation, measuring a dew point of the sample gas using a dew point meter, removing moisture in the sample gas by using a moisture trap according to a dew point, and removing particulate material by using a filter, a gas detection module including a means of verify the validation of warning by detecting gaseous decomposition products in the sample gas passed through the gas preprocessing module, and letting the sample gas pass the hydrocarbon trap which absorbs and removes gaseous decomposition products, target of detection.

The gas preprocessing module comprises extraction valve for extracting the sample gas from a generator, a dew point meter for measuring moisture contents in a hydrogen gas, a filter for removing particulate material in hydrogen gas, flow controller for controlling a hydrogen gas flow, the first control valve for changing a hydrogen gas flow, the first flow pipe for letting hydrogen gas bypass without letting it pass through a moisture trap, and a moisture trap for removing moisture in a hydrogen gas. And the gas detection module comprises the second control valve for changing hydrogen gas flow, the second flow pipe for letting the hydrogen gas bypass without letting it pass through a hydrocarbon trap, a hydrocarbon trap for absorbing and removing gaseous decomposition products in a hydrogen gas, a filter for removing particulate material in the hydrogen gas, a detection sensor for detecting gaseous decomposition products in the hydrogen gas, and a exhaust valve for exhausting hydrogen gas. Thus contamination and deterioration of detection sensitivity of the sensor is prevented by removing moisture and oil in the hydrogen gas, and reliability of the device can be further improved by enabling verification of occurrence of the actual situation when an alarm is issued.

At this time, the moisture trap is preferably filled with calcium chloride absorbent to pass the detection target gas and remove only the oil and moisture.

And generator condition monitoring method using gaseous decomposition products sensor according to the present invention comprises the first step of letting the sample gas bypass or pass through a moisture trap depending on the amount of moisture in the sample gas, the second step of bypassing a hydrocarbon trap in case gaseous decomposition products (VOCs) in the sample gas detected by a detection sensor is below a standard value and passing through the hydrocarbon trap for a while in case gaseous decomposition products (VOCs) in the sample gas detected by a detection sensor is above the standard value, and the third step of determining the actual situation occurs if the detection sensor indicates "0" while the sample gas passes through the hydrocarbon trap and restores back to the former indication value while the sample gas bypasses the hydrocarbon trap and determining device has problem if a detection sensor keeps indicating high while the sample gas passes through the hydrocarbon trap.

Generator condition monitoring device and method using gaseous decomposition products sensors according to the present invention have the effect as follows.

First, malfunction of the device can be promptly determined by an operator when an alarm is issued. Thus monitoring device will have higher reliability.

Secondly, life of the moisture trap can be prolonged and sensitivity deterioration of detection sensor is prevented by letting hydrogen gas pass through an oil and a moisture trap only when introduced moisture contents are larger than the standard value.

Thirdly, the oil and moisture in a hydrogen gas are removed in a preprocessing module without using water.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF SPECIFIC EMBODIMENTS

Although the present invention is described in conjunction with the preferred embodiments which illustrate the technical spirit of the present invention, it will be apparent to those skilled in the art that the present invention is not limited only to the illustrated and described configurations and operations themselves but a lot of variations and modifications are possible without departing from the scope of the spirit of the invention. Accordingly, all of appropriate variations, modifications and equivalents are considered to pertain to the scope of the present invention.

Hereinafter, detailed description will be given of the present invention with reference to the accompanying drawings.

First overall structure of a generator condition monitoring device using gaseous decomposition products sensor is briefly described, and specific feature of respective structure and organic functional relationship between structures are described in detail. Last, the monitoring method using the monitoring device according to the present invention is described.

Figure 1:
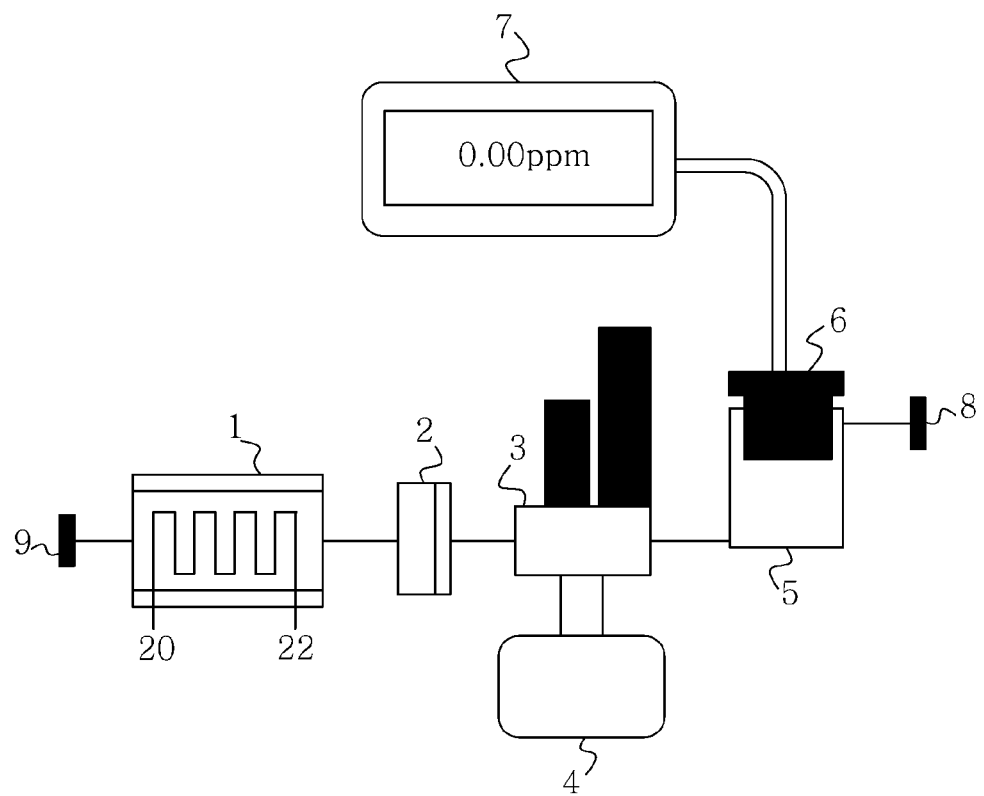
FIG. 1 is a diagram illustrating the prior art.
Figure 2:
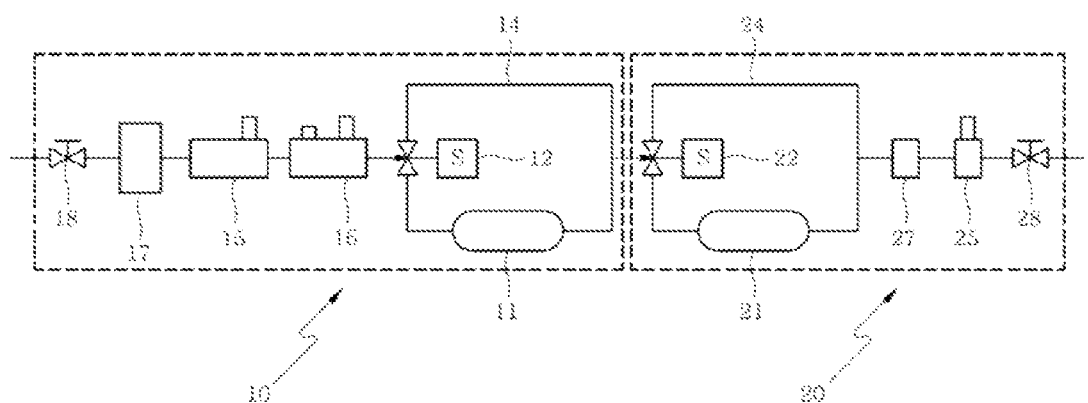
FIG. 2 is a diagram illustrating the monitoring device of the present invention.

FIG. 2 shows the structure of generator condition monitoring device using gaseous decomposition products sensor according to the present invention.

According to FIG. 2, the monitoring device of the present invention comprises a gas preprocessing module 10 for extracting some hydrogen gas circulating inside generator in operation and removing oil and moisture, and a gas detection module 20 for measuring the concentration of gaseous decomposition products from the sample gas from which moisture and oil were removed.

The dotted line block in the left side of FIG. 2 shows a gas preprocessing module 10, and the dotted line block in the right side of FIG. 2 shows a gas detection module 20.

The gas preprocessing module 10 comprises a filter 17 for removing particulate material in a hydrogen gas extracted in generator through a extraction valve 18, a dew point meter 15 for detecting moisture contents in a hydrogen gas, flow controller 16 for controlling a gas flow, and the first control valve 12 for letting hydrogen gas bypass a moisture trap 11 and flow to the first flow pipe or letting a hydrogen gas pass through moisture trap 11 depending on the amount of moisture in hydrogen gas. And the gas detection module 20 comprises the second control valve 22 for letting a hydrogen gas flow to the second flow pipe or a hydrocarbon trap 21 depending on warning-issuing standard, a filter 27 for removing particulate material in a hydrogen gas, a detection sensor 25 for detecting gaseous decomposition products in a hydrogen gas.

Herein, a moisture trap 11 is formed as sealed type trap filled with a calcium chloride absorbent.

Detailed feature and mutual relation of respective composition of generator condition monitoring device using gaseous decomposition products sensor according to the present invention are described below in detail with reference to FIG. 2.

Some of hydrogen gas (a sample gas) circulating inside generator flows into a gas preprocessing module 10. The sample gas from which particulate materials were removed in a filter 17 passes through the dew point meter 15. And then depending on moisture contents in the sample gas, the sample gas is controlled in constant flow to pass through the first flow pipe by the first control valve 12 or pass through the moisture trap 11. That is, in case the dew point of the sample gas is below the standard value, the sample gas is controlled to flow into the first flow pipe. And in case the dew point is above the standard value, the sample gas is controlled to pass through a moisture trap 11 by the first control valve 12. Thereby, life of a moisture trap 11 is prolonged. At this time, the dew point standard value of a dew point meter is to be preferably below 5° C. (relative humidity 35% or less).

Particles larger than 0.001 μm are preferably removed in a filter 17, oil or moisture is also removed together with particles.

A moisture trap 11 is preferably filled with Calcium Chloride absorbent. Absorbents other than Calcium Chloride interferes measurement of detection sensor since other absorbents absorb target gas for detection as well as oil and moisture.

The sample gas passes through a preprocessing module 10 and bypasses a hydrocarbon trap 21 and flow into detection sensor 25 through the second flow pipe by the second control valve 22 in case the concentration of gaseous decomposition products (VOCs) is below warning standard. And in case the concentration of gaseous decomposition products (VOCs) is above warning standard, the sample gas flows into detection sensor 25 after passing through the hydrocarbon trap 21 for awhile (about 5 mins). Herein, a filter 27 is installed in the front end of a detection sensor 25 to remove particulate material which can outflow in a hydrocarbon trap 21. While the sample gas passes through the hydrocarbon trap 21, gaseous decomposition products (VOCs) are absorbed and removed by absorbents filled in the hydrocarbon trap 21. Thus, the indication value of the detection sensor 25 indicates "0". At this time, if the indication value of the detection sensor 25 keeps indicating above the standard value, it means there is abnormality of the detection device. And if the indication value indicates "0" while passing through the hydrocarbon trap 21 and the indication value of the detection sensor is restored back to the former indication value with the hydrocarbon trap 21 bypassed, it can be seen as the actual situation.

Thereby, provided is a means for an operator to determine whether an alarm is issued due to the actual situation or abnormality of the device.

For reference, detection sensor 25 at this time is not particulate material detection sensor i.e. ICD (Ion Chamber Detector) but gaseous detection sensor i.e. PID sensor (Photo Ionization Detector) or semiconductor sensor.

On the other hand, a hydrocarbon trap 21 embeds filling material which absorbs gaseous decomposition products (VOCs), i.e. detection target. Filling material is preferably made of any one of a molecular sieve 13×, molecular sieve 4×, silicagel or any combination thereof.

The sample gas passing through a detection sensor 25 is to be returned back inside generator by the emission valve 28 or the like means.

Generator condition monitoring method using a generator condition monitoring device using gaseous decomposition products sensor according to the present invention is briefly described here to avoid overlapped description since much of the related information was described beforehand.

Figure 3:
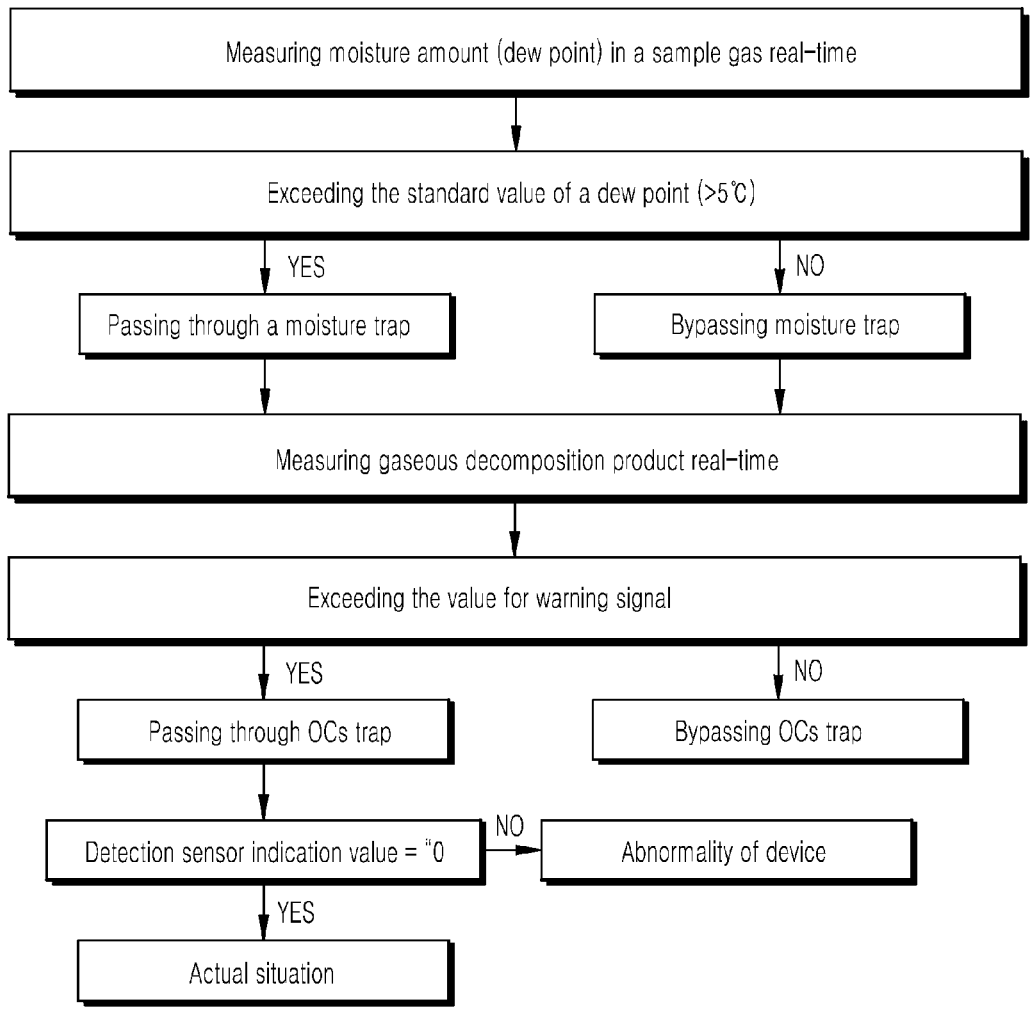
FIG. 3 is a block diagram illustrating the monitoring method in sequence using the monitoring device of the present invention.

FIG. 3 shows a block diagram illustrating the sequence of monitoring method. The block is illustrated in 8 steps. The first to the third block corresponds to the first step in the monitoring method, the fourth to the sixth block corresponds to the second step, and the seventh to the eighth block corresponds to the third step.

Thus, monitoring method includes a first step of letting the sample gas bypass or pass through a moisture trap and a second step of bypassing a hydrocarbon trap 21 in case gaseous decomposition products (VOCs) in the sample gas detected by a detection sensor 25 are below a standard value and passing through a hydrocarbon trap 21 for awhile in case gaseous decomposition products (VOCs) in the sample gas detected by a detection sensor are above a standard value.

And it includes a third step of diagnosis to determine the actual situation occurs if a detection sensor 25 indicates "0" while the sample gas passes through a hydrocarbon trap 21 and restores back to the conventional indication value when the sample gas bypasses a hydrocarbon trap 21 and to determine the device has problem if detection sensor 25 keeps indicating a high value while the sample gas passes through hydrocarbon trap 21.

Accordingly, the present invention reduces warning to minimum issued by abnormality of device and provides a means for generator operators to work safely.

On the other hand, the present invention is described with limitation that only a hydrogen gas is used as a coolant in a generator, the present invention can be applied to any device for monitoring abnormality of equipment in various motors using coolants other than a hydrogen gas.

Although the present invention has been described in conjunction with the preferred embodiments which illustrate the technical spirit of the present invention, it will be apparent to those skilled in the art that the present invention is not limited only to the illustrated and described configurations and operations themselves but a lot of variations and modifications are possible without departing from the scope of the spirit of the invention. Accordingly, all of appropriate variations, modifications and equivalents are considered to pertain to the scope of the present invention.

What is claimed is:

1. A device for monitoring generator conditions using gaseous decomposition products sensor comprising:
    a gas preprocessing module for extracting some (a sample gas) of a hydrogen gas circulating inside a generator in operation, removing moisture in the sample gas by using a moisture trap depending on a dew point of the sample gas which is measured by a dew point meter, and removing particulate material by using a filter; and
    a gas detection module for detecting gaseous decomposition products in the sample gas which passed through the gas preprocessing module by a detection sensor, comprising a means for verifying validity of warning by letting the sample gas pass through a hydrocarbon trap for absorbing and removing the detected gaseous decomposition products if exceeding warning standard, i.e. an alarm is issued.

2. The device according to claim 1, wherein the moisture trap is of a sealed type filled with Calcium Chloride.

3. The device according to claim 1, wherein the gas preprocessing module is characterized by passing through or bypassing a moisture trap by a first control valve depending on the dew point of the sample gas.

4. The device according to claim 1, wherein the means for verifying validity of warning identifies abnormality of the device by letting the sample gas bypass or pass through a hydrocarbon trap by a second control valve according to indication value of a detection sensor.

5. The device according to claim 4, wherein the hydrocarbon trap contains filler absorbing gaseous decomposition products in the sample gas.

6. The device according to claim 5, wherein the filler is any one of molecular sieve 13x, molecular sieve 4x, silicagel, and deirite.

7. A method for monitoring generator conditions by a device using gaseous decomposition products sensor comprising:
    a first step of letting a sample gas bypass or pass through a moisture trap depending on the amount of moisture in the sample gas;
    a second step of bypassing a hydrocarbon trap in case gaseous decomposition products (VOCs) in the sample gas detected by a detection sensor is below a standard value and passing through a hydrocarbon trap during a predetermined time period in case gaseous decomposition products (VOCs) in the sample gas detected by a detection sensor is above the standard value; and
    a third step of determining that the gaseous decomposition products (VOCs) in the sample gas is above the standard value if the detection sensor indicates "0" while the sample gas passes through the hydrocarbon trap and restores back to a conventional indication value while the sample gas bypasses the hydrocarbon trap and determining that the device has a problem if the detection sensor keeps indicating a high value while the sample gas passes through the hydrocarbon trap.

* * * * *